(12) United States Patent
Pays et al.

(10) Patent No.: US 11,376,202 B2
(45) Date of Patent: Jul. 5, 2022

(54) MASCARA COMPOSITION CONTAINING A TETRAHYDROXYPROPYL ETHYLENEDIAMINE ESTER

(71) Applicant: LVMH RECHERCHE, Saint Jean de Braye (FR)

(72) Inventors: Karl Pays, Saint Maurice (FR); Yohann Bichon, Maisons-Alfort (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 314 days.

(21) Appl. No.: 16/618,045

(22) PCT Filed: Dec. 19, 2018

(86) PCT No.: PCT/FR2018/053429
§ 371 (c)(1),
(2) Date: Nov. 27, 2019

(87) PCT Pub. No.: WO2019/122727
PCT Pub. Date: Jun. 27, 2019

(65) Prior Publication Data
US 2020/0093723 A1  Mar. 26, 2020

(30) Foreign Application Priority Data

Dec. 21, 2017 (FR) .................................. 1762856

(51) Int. Cl.
| | |
|---|---|
| *A61K 8/41* | (2006.01) |
| *A61K 8/06* | (2006.01) |
| *A61K 8/36* | (2006.01) |
| *A61K 8/92* | (2006.01) |
| *A61Q 1/10* | (2006.01) |

(52) U.S. Cl.
CPC .................. *A61K 8/41* (2013.01); *A61K 8/06* (2013.01); *A61K 8/361* (2013.01); *A61K 8/92* (2013.01); *A61Q 1/10* (2013.01)

(58) Field of Classification Search
None
See application file for complete search history.

(56) References Cited

U.S. PATENT DOCUMENTS

| | | |
|---|---|---|
| 5,747,013 A | 5/1998 | Mougin et al. |
| 2003/0224025 A1 | 12/2003 | Gotsche et al. |
| 2005/0069510 A1 | 3/2005 | Drohmann et al. |
| 2006/0165620 A1 | 7/2006 | Bujard et al. |
| 2015/0250703 A1* | 9/2015 | Ilekti .................... A61K 8/06 424/70.7 |
| 2016/0083333 A1 | 3/2016 | Schwab et al. |

FOREIGN PATENT DOCUMENTS

| | | |
|---|---|---|
| EP | 0023978 | 2/1981 |
| EP | 0663202 | 7/1995 |
| EP | 0928607 | 7/1999 |
| EP | 2356981 | 8/2011 |
| EP | 3228304 | 10/2017 |
| FR | 2996767 | 4/2014 |
| JP | 2005513234 | 5/2005 |
| JP | 5628019 B2 | 11/2014 |
| JP | 2016069374 | 5/2016 |
| WO | 2015177113 | 11/2015 |

OTHER PUBLICATIONS

"Tinted Dual Brow," May 2016, abstract No. Database accession No. 3974221, Retrieved from: GNPD [online], Mintel XP002780794 (3 pages).

International Search Report and Written Opinion issued for International Patent Application No. PCT/FR2018/053429, dated Apr. 10, 2019, 14 pages including English translation of Search Report.

* cited by examiner

*Primary Examiner* — Robert A Wax
*Assistant Examiner* — Randeep Singh
(74) *Attorney, Agent, or Firm* — Hamre, Schumann, Mueller & Larson, P.C.

(57) ABSTRACT

The subject of the invention is a wax-in-water emulsion containing at least one fatty acid ester of tetramethylpropylethylenediamine, which is intended to replace triethanolamine, known to decompose into nitrosamines when the preserved emulsion is packaged in a thermoplastic material. Moreover, this emulsion has the advantage of gaining shade depth and fluidity, especially in products rich in waxes.

Figure 1:
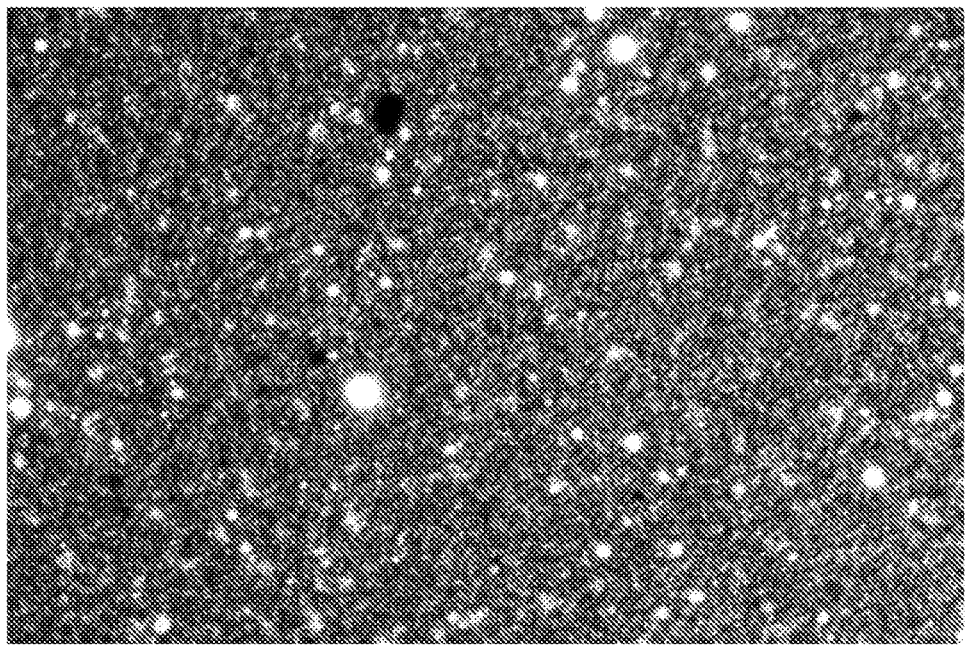

13 Claims, 1 Drawing Sheet ature of the emulsion
MASCARA COMPOSITION CONTAINING A TETRAHYDROXYPROPYL ETHYLENEDIAMINE ESTER The present application relates to the field of making up or caring for the eyelashes, in particular to the field of cream mascaras and relates more specifically to a cosmetic composition that can be applied to keratin fibers.

The invention relates more specifically to a mascara containing a high amount of waxes emulsified in an aqueous phase with a fatty acid ester of tetrahydroxypropyl ethylenediamine (THPE).

PRIOR ART

Wax-in-water mascaras containing triethanolamine (TEA) esters such as triethanolamine stearate are recognized for their soft, creamy and smooth application quality. Triethanolamine esters are formed during the process of preparing the mascara by reaction of a fatty acid or a mixture of fatty acids with triethanolamine.

However, TEA leads to a high risk of formation of nitrosamines during the storage and use of the mascara preserved in a packaging. TEA can in fact react with components of the packaging to release nitrosamines such as NDELA (N-nitrosodiethanolamine), so that its use in numerous products is regulated. Cosmetic products, for example, must have an NDELA content of less than 10 ppb in order to adhere to the regulations in the main European countries.

Several proposals to partially or totally replace TEA with other hydroxylated amines so as to form fatty acid esters have been developed, but the mascaras obtained have drawbacks.

This is the case in particular with wax-in-water mascaras containing aminomethyl propanediol (AMPD) esters which are less creamy and drier on application when TEA is completely replaced with AMPD. Such formulas are for example described in document EP 3 228 304.

Other amines, such as tromethamine, have also been evaluated, but the tests in which TEA is replaced with these amines have not made it possible to totally remove it from the formulas while at the same time retaining a satisfactory makeup result.

The need to have cream mascaras in wax-in-water emulsion containing fatty acid esters which are not capable of releasing nitrosamines during their lifetime, and which have a smooth texture on application, thus persists.

More specifically, a mascara is sought which is devoid of triethanolamine esters, which have application qualities at least equivalent to those of the mascaras containing said triethanolamine esters, and which do not suffer from the disadvantages of those that have been developed by triethanolamine replacement.

The inventors have found, surprisingly, that fatty acid esters of tetrahydroxypropyl ethylenediamine formulated in wax-in-water emulsions make it possible to obtain smooth and creamy products which are pleasant to use without the risk of nitrosamine release.

The fatty acid esters of tetrahydroxypropyl ethylenediamine can totally replace the triethanolamine esters in the existing architectures while at the same time preserving the same properties, or even improving some of them.

It has in particular been discovered that the fatty acid esters of tetrahydroxypropyl ethylenediamine make it possible to provide new mascara textures, that are original by virtue of their sensoriality, their application qualities and their makeup results.

The texture can be more fluid, which makes the application slide better and more pleasant. Although the emulsion is more fluid, the charging of the eyelashes remains equivalent, which is very surprising.

The formula can also be more adherent, which improves the persistence of the product on the eyelashes over time.

Finally, the composition makes it possible to obtain deeper shades, in particular blacks that are more intense.

Tetrahydroxypropyl ethylenediamine has already been incorporated into cosmetic composition at low concentration in order to perform the function of pH adjustment. However, in these compositions, tetrahydroxypropyl ethylenediamine cannot form the necessary significant amounts of esters in the mascaras in emulsion in order to stabilize the waxes in an aqueous phase.

DESCRIPTION OF THE INVENTION

A subject of the invention is thus a cosmetic composition for caring for or making up the eyelashes or the eyebrows, comprising waxes in emulsion in an aqueous phase and at least one ester obtained by reacting a linear and saturated fatty acid comprising from 16 to 20 carbon atoms, and tetrahydroxypropyl ethylenediamine, the fatty acid representing from 1.0 to 10.0% by weight and the amine representing from 0.1 to 8.0% by weight, and the mole ratio between the fatty acid and the amine being between 0.9 and 5.

The fatty acid may represent from 1.0 to 10% by weight, preferably from 2.0 to 8.0% by weight, more preferentially from 2.5 to 5.0% by weight, and even more preferentially from 4.0 to 6.0% by weight, relative to the weight of the composition.

The amine may represent from 0.1 to 8.0% by weight, preferably from 1.0 to 8.0% by weight or else from 1.0 to 6.0% by weight, more preferentially from 3.0 to 8.0% by weight, even more preferably from 3.0 to 7.0% by weight, even more preferentially from 3.0 to 6.0% by weight, and even more preferentially from 3.0 to 4.5% by weight, relative to the weight of the composition.

The mole ratio between the linear and saturated fatty acid and the tetrahydroxypropyl ethylenediamine is preferably between 0.9 and 4.0, preferably between 1.0 and 3.0, and more preferably between 1.1 and 2.0. The fatty acid is preferably used in excess such that it contributes to the structuring of the fatty phase.

In the present description, the percentages by weight are expressed relative to the weight of the emulsion unless otherwise mentioned.

The composition preferably comprises less than 1% by weight of a compound or of a mixture of compounds chosen from a triethanolamine ester, an aminomethyl propanediol ester, and a tromethamine ester, which are capable of harming the performance qualities of the mascara.

The invention also describes a cosmetic composition for caring for or making up the eyelashes or the eyebrows in the form of a wax-in-water emulsion comprising an amount of compounds bearing an amine function capable of breaking down into nitrosamines in an amount of less than 10 ppb, characterized in that it comprises an ester of a linear and saturated fatty acid having from 16 to 20 carbon atoms and of tetrahydroxypropyl ethylenediamine, said ester being in an amount sufficient to obtain a viscosity, the value of which is at least 20% less than the viscosity of an identical composition comprising a fatty acid ester of an amine chosen from triethanolamine, tromethamine and aminopropanediol.

The composition is advantageously devoid of esters of a linear and saturated fatty acid with an amine chosen from triethanolamine, aminopropanediol and tromethamine.

The linear and saturated fatty acid may be stearic acid, palmitic acid or behenic acid. According to one embodiment, a mixture of stearic acid and palmitic acid, for example in a weight ratio of between 80/20 and 20/80, and advantageously in the weight ratio 50/50, is used. One particular embodiment comprises the equal-weight mixture of stearic acid and palmitic acid.

The IUPAC nomenclature of tetrahydroxypropyl ethylenediamine is N,N,N',N'-tetrakis(2-hydroxypropyl)ethylenediamine and the INCI name is Tetrahydroxypropyl Ethylenediamine. It is sold in particular under the brands Neutrol® TE, Lutropur® Q75 from BASF, and Adeka Carpol® MD100 from Adeka.

The amount of the fatty acid ester of tetrahydroxypropyl ethylenediamine is preferably sufficient to obtain a percentage decrease in the viscosity of the mascara which is greater than a value chosen from the group consisting of 10%, 15%, 20%, 25%, 30%, 35% and 40%, relative to a mascara of identical composition wherein the tetrahydroxypropyl ethylenediamine ingredient used to produce the mascara is replaced with triethanolamine.

The composition according to the invention has a fluid texture: its viscosity is preferably less than 250 000 mPa·s, for example between 150 000 mPa·s and 230 000 mPa·s, preferably between 140 000 mPa·s and 210 000 mPa·s. The viscosity of the composition can be measured at 25° C. using a Rheomat® 180 (the company LAMY) equipped with an MS-R1, MS-R2, MS-R3, MS-R4 or MS-R5 spindle chosen as a function of the consistency of the composition, rotating at a rotation speed of 200 rpm. The measurement is taken after 10 min of rotation.

The fatty acid ester of THPE performs the function of an anionic surfactant with an HLB greater than 8. In the present invention, the HLB values are the Griffin values at 25° C.

At least one nonionic surfactant, the HLB of which is less than 8, can optionally be combined with said ester, in particular when the amount of waxes in the composition is greater than 20% by weight. This surfactant may be chosen from the group consisting of:
  monosaccharide esters and ethers;
  esters of fatty acids, in particular $C_8$-$C_{24}$, and preferably $C_{16}$-$C_{22}$ fatty acids, and of a polyol, in particular of glycerol or of sorbitol, preferably of glycerol, such as glyceryl stearate;
  oxyalkylenated alcohols comprising less than 10 oxyalkylene units, better still less than 5 oxyalkylene units, in particular oxyethylene and/or oxypropylene units.

An oxyethylenated alcohol comprising less than 5 oxyalkylene units may be the compound with the INCI name Steareth-2.

The composition may also contain a mixture of surfactants comprising the fatty acid ester of THPE, at least one nonionic surfactant, the HLB of which is less than 8 as described above, and at least one nonionic surfactant, the HLB of which is greater than 8. This combination is particularly advantageous when the wax content in the composition is greater than 30% by weight.

Said surfactant may be chosen from:
  fatty alcohols comprising from 8 to 24 carbon atoms (such as stearyl alcohol) which comprise 20 oxyethylene units (with the INCI name Steareth-20, the compound with the INCI name Ceteareth-30 and the compound having the INCI name Pareth-7),
  PEG-40 monostearate,
  fatty acid esters comprising 30 oxyethylene units, such as polyoxyethylenated glyceryl stearate comprising 30 oxyethylene units, polyoxyethylenated glyceryl oleate comprising 30 oxyethylene units, polyoxyethylenated glyceryl cocoate comprising 30 oxyethylene units, polyoxyethylenated glyceryl isostearate comprising 30 oxyethylene units, polyoxyethylenated glyceryl laurate comprising 30 oxyethylene units, and
  polyoxyethylenated sorbitan esters, such as polysorbate 60.

The composition may contain an anionic surfactant having an HLB value greater than or equal to 8, such as alkyl phosphates and alkyl sulfates. In one particular embodiment of the invention, the composition is devoid of anionic surfactant.

The surfactants preferentially used in composition according to the invention are chosen for example from oxyethylenated and/or oxypropylenated ethers, fatty acid esters of polyethylene glycol, polyethylene glycol/polypropylene glycol polycondensates, fatty acid esters of glycerol, such as glyceryl stearate, fatty acid esters of sorbitol, fatty acid esters of sorbitan, sucrose esters and sucrose ethers.

According to one particular embodiment, the composition contains a high amount of wax(es), preferably between 15 and 25% by weight. These particular compositions advantageously make it possible to deposit a great deal of product from the first pass of the brush on the eyelashes, in order to better coat the eyelashes, to provide volume that is immediately noticeable by the user, and to increase the persistence of the makeup over time.

However, the wax-in-water emulsions with a high wax content of the prior art can lack fluidity, so that the amount of product deposited on the eyelashes becomes too great and the coating of the eyelashes is less uniform.

The introduction of an ester of linear fatty acids and of tetrahydroxypropyl ethylenediamine into wax-in-water emulsions containing large amounts of solid compounds, such as waxes, is thus particularly advantageous since it makes it possible to counteract the increase in consistency introduced by these compounds by reducing the viscosity very significantly. In this type of architecture, the composition of the invention thus entirely advantageously makes it possible to propose cream mascaras which provide immediate volume, a lengthening and a persistence over time with high performance qualities, after a smooth and uniform application of the product.

Use may be made of any wax known by those skilled in the art of cosmetics. The wax may for example be chosen from:
  alkane waxes, also referred to as apolar, chosen from waxes resulting from oil distillation, such as microcrystalline waxes and certain paraffin waxes; synthetic waxes obtained by polymerization of methylene, of ethylene or of propylene, such as polymethylene wax, polyethylene wax, polypropylene wax, ethylene/propylene copolymer wax and ethylene/hexene copolymer wax; Fischer Tropsch waxes; ozokerite wax; and ceresin obtained by refining ozokerite,
  silicone waxes, and
  waxes which are neither silicone waxes nor alkane waxes, also referred to as polar, such as for example beeswax, rice bran wax, carnauba wax, candelilla wax, ouricurry wax, Japan wax, berry wax, sumac wax, montan wax, esparto wax, cork fiber wax, sugarcane wax, orange wax, lemon wax, laurel wax, waxes obtained by hydrogenation of animal or plant oils having linear or branched, $C_8$-$C_{32}$ fatty chains, such as jojoba oil, sunflower oil, castor oil, coconut oil, lanolin oil, olive oil esterified with stearyl alcohol, castor oil esterified with cetyl alcohol.

According to one embodiment of the invention, the waxes represent from 10 to 35% by weight, preferably from 15% to 35% by weight, more preferably from 18% to 28% by weight, relative to the weight of the composition.

In one particular embodiment, the composition contains a mixture of apolar wax and polar wax.

In another embodiment, the composition contains 10 to 20% by weight of a wax, the melting point of which is greater than or equal to 70° C. The melting point may be measured by any method known to those skilled in the art. For the purposes of the present invention, the term "melting temperature" or "melting point" of a compound is intended to mean in particular one of the following parameters: the melting point corresponding to the beginning of the melting of this compound or the temperature corresponding to the endothermic peak of the compound, it being possible for these parameters to be measured by D.S.C. (Differential Scanning Calorimetry) according to standard ISO 11357-3.

A wax, the melting point of which is greater than or equal to 70° C., used in the context of the invention may be a paraffin wax, the melting point of which ranges from 62° C. to 65° C., a candelilla wax, a beeswax or a carnauba wax, the melting point of which ranges from 78 to 85° C. The melting point varies as a function of the process for producing the wax and of the method used to measure it.

The composition may contain in particular the mixture of at least one wax, the melting point of which is greater than or equal to 70° C., and at least one wax, the melting point of which is less than 70° C., one of the waxes being an apolar wax and the other being a polar wax.

The composition may contain at least one polymer which performs the function of a texturing, film-forming or gelling agent. The polymer may in particular be intended to increase the coating of the eyelashes, the lengthening of the eyelashes and/or the curving thereof.

The amount of polymer can range from 2 to 20%, preferably from 3 to 10% by weight relative to the weight of the composition.

Among the polymers that can be envisioned are polybutene, ethylcellulose and vinylpyrrolidone (VP) copolymers such as VP/eicosene or VP/hexadecene, hydrogenated polydecene, nonvolatile silicone oils, in particular phenyl trimethicones, and mixtures thereof.

Among the polymers, mention may also be made of cellulose polymers such as hydroxyethylcellulose, vinyl polymers such as polyvinylpyrrolidones, gums arabic, guar gum, xanthan derivatives, aqueous dispersions of acrylate copolymers, and mixtures thereof.

The total amount of polymers and of waxes in the composition is preferably between 15% and 35% of the composition.

The mascara composition comprises pigments representing from 5 to 20% by weight, for example from 8 to 15% by weight of the composition.

The pigments are preferably chosen from titanium dioxide, zinc oxides, (black, yellow or red) iron oxides, manganese violet, ultramarine blue, chromium hydrate and ferric blue, and metal powders such as aluminum powder or copper powder. Among the organic pigments, mention may be made of carbon black, D & C pigments, and lakes. Mention may also be made of reflective pigments and nacre pigments.

The liquid phase represents for example from 30% to 60% by weight, preferably from 40% to 55% by weight, relative to the weight of the mascara composition.

The liquid phase may contain water, volatile oils and polyols such as butylene glycol. The oils may be chosen from volatile dimethicones, cyclomethicones, isododecane, isohexadecane or isodecane.

According to one embodiment of the invention, the liquid phase represents from 40% to 55% by weight, the waxes represent from 20% to 25% by weight, and the pigments represent from 8 to 12% by weight.

The compositions of the invention may contain, in addition to the ingredients described above, adjuvants that are customary in the mascara formulation field, such as hydrophilic or lipophilic gelling agents, active agents, nonvolatile oils, fatty compounds in paste form, preserving agents, antioxidants, pH adjusters and fragrances.

The nonvolatile oils may be chosen from liquid paraffin, isotridecyl isononanoate, isostearyl neopentanoate, tridecyl neopentanoate and cetyl octanoate. Use is preferably made of nonvolatile oils of plant origin, such as castor oil, argon oil, or almond oil, which may also serve as an active agent.

The description of the ingredients which are part of the composition of the invention can be supplemented from the content of application FR 2 996 767.

The invention is illustrated by the following examples.

Example 1, Comparative Example 2 and Comparative Example 3

Three mascara formulas were prepared using the ingredients in the proportions indicated in table 1 below.

TABLE 1

| | Composition of the mascaras | | | |
|---|---|---|---|---|
| Phase | Ingredients (INCI name) | Example 1 | Comparative example 2 | Comparative example 3 |
| A1 | WATER | qs 100 | qs 100 | qs 100 |
| A1 | PRESERVATIVES | 2.90 | 2.90 | 2.90 |
| A1 | TRIETHANOLAMINE | — | 2.00 | — |
| A1 | AMINOMETHYL PROPANEDIOL (AMPD ULTRA PC) | — | — | 1.40 |
| A1 | TETRAHYDROXYPROPYL ETHYLENEDIAMINE (NEUTROL TE) | 3.90 | — | — |
| A2 | HYDROXYETHYLCELLULOSE | 0.60 | 0.60 | 0.60 |
| A2 | ACACIA SENEGAL GUM | 2.00 | 2.00 | 2.00 |
| A2 | PVP (PVP K30) | 0.50 | 0.50 | 0.50 |
| B1 | STEARIC ACID | 2.00 | 2.00 | 2.00 |
| B1 | PALMITIC ACID | 2.00 | 2.00 | 2.00 |
| B1 | VP/EICOSENE COPOLYMER (ANTARON V 220 F) | 2.00 | 2.00 | 2.00 |
| B1 | POLYBUTENE (POLYBUTENE M 2000) | 2.00 | 2.00 | 2.00 |
| B1 | SYNTHETIC BEESWAX (KESTER WAX K 82P) | 12.00 | 12.00 | 12.00 |
| B1 | GLYCERYL STEARATE (CUTINA GMS-V) | 4.00 | 4.00 | 4.00 |
| B1 | CERA CARNAUBA | 4.00 | 4.00 | 4.00 |
| B1 | PARAFFIN | 10.00 | 10.00 | 10.00 |
| B2 | BLACK IRON OXIDE | 10.00 | 10.00 | 10.00 |

In order to perform a reliable comparison, the total amount of stearic acid and of palmitic acid was kept constant for the two tests, and the amount of THPE was adjusted to obtain an equal THPE/(fatty acids) mole ratio.

Preparation Process

Prepare the aqueous phase A1, stir using a Staro mixer in a water bath at 85° C.

Add the gelling agents of aqueous phase A2 into A1 with stirring.

Prepare the fatty phase B1, place in a water bath at 85° C. and with stirring using a Staro mixer.

Once phase B1 has melted, add the mixture of the pigments and fillers B2 into B1 with stirring, and disperse for 30 min.

Emulsify A in B with vigoruosu stirring using a Staro mixer at 85° C. for 5 min, then remove the water bath.

Leave to cool to 30° C. while gradually reducing the stirring.

Observations Under a Microscope

Figure 2:
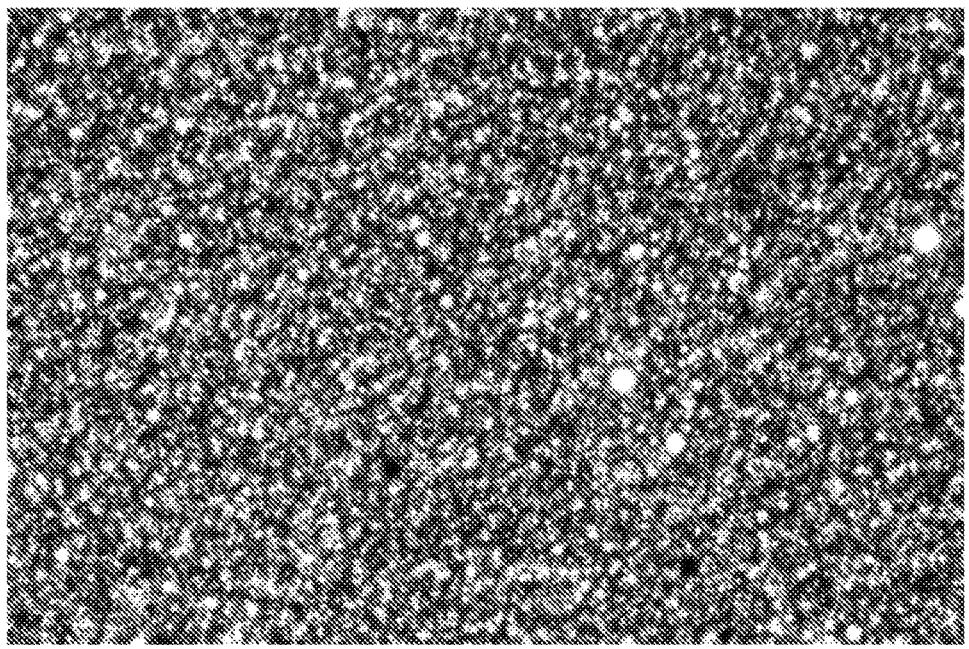

The compositions of example 1 and of comparative example 2 were observed under a microscope at a magnification of 100. FIG. 1 and FIG. 2 show the images obtained.

The dispersions of the two compositions are homogenous, uniform and quite tight; the waxes and the pigments are well dispersed.

The THPE ester makes it possible to obtain dispersions that are as fine as those obtained with the triethanolamine ester.

Measurement of Viscosity and of pH

Method of Measurement

Each formula was packaged in a 120 mL pill bottle and left to stand for 24 h in an incubator at a temperature of 25° C.

Equipment: Rheolab QC
Measuring spindle: ST22-2V
Rotation 50 rpm for 7 min

Results

The values measured are presented in table 2 below.

The viscosity of the mascara of the invention is about 150 000 to 160 000 cPs, while that of the mascara containing triethanolamine stearate is about 200 000 cPs.

TABLE 2

Physicochemical characterization

|  | Example 1 | Comparative example 2 | Comparative example 3 |
|---|---|---|---|
| VISCOSITY (24 h) CPS | 156 900 | 206 700 | 181 400 |
| pH (24 h) | 8.61 | 8.45 | 8.94 |

Makeup Result

The results are presented in table 3 below.

TABLE 3

Makeup and application qualities

|  | Example 1 | Comparative example 2 | Comparative example 3 |
|---|---|---|---|
| CREAMY | + | ++ | − |
| VOLUME | ++ | ++ | + |
| EYELASH SUPPLENESS | + | + | − |
| ADHESION | +++ | ++ | − |

Legend:
− insufficient
+ medium result
++ very good
+++ excellent

The composition of the invention is more fluid and more adherent than the prior art controls containing triethanolamine stearate and palmitate, so that the eyelashes are made up in a single pass of the brush. The mascara is more pleasant to apply and the perceived black shade is deeper. The amounts of product deposited on the eyelashes are equivalent for all the compositions.

Example 4, Comparative Example 5 and Comparative Example 6

Three mascara formulas were prepared using the ingredients in the proportions indicated in table 4 below.

TABLE 4

Composition of the mascaras

| Phase | Ingredients (INCI name) | Example 4 | Comparative example 5 | Comparative example 6 |
|---|---|---|---|---|
| A1 | WATER | qs 100 | qs 100 | qs 100 |
| A1 | PRESERVATIVES | 1.20 | 1.20 | 1.20 |
| A1 | TRIETHANOLAMINE | — | 2.25 | — |
| A1 | AMINOMETHYL PROPANEDIOL (AMPD ULTRA PC) | — | — | 1.59 |
| A1 | TETRAHYDROXYPROPYL ETHYLENEDIAMINE (ADEKA CARPOL MD-100) | 4.42 | — | — |
| A2 | ACACIA SENEGAL GUM | 1.70 | 1.70 | 1.70 |
| A2 | HYDROXYETHYLCELLULOSE | 1.00 | 1.00 | 1.00 |
| B1 | STEARIC ACID | 2.25 | 2.25 | 2.25 |
| B1 | PALMITIC ACID | 2.25 | 2.25 | 2.25 |
| B1 | PARAFFIN | 10.90 | 10.90 | 10.90 |
| B1 | VP/EICOSENE COPOLYMER (ANTARON V 220 F) | 1.90 | 1.90 | 1.90 |
| B1 | BIS DIGLYCERYL POLYACYLADIPATE-2 (SOFTISAN 649 MB) | 2.80 | 2.80 | 2.80 |
| B1 | POLYBUTENE (POLYBUTENE M 2000) | 5.60 | 5.60 | 5.60 |
| B1 | CANDELILLA CERA | 0.90 | 0.90 | 0.90 |
| B1 | BEESWAX | 6.50 | 6.50 | 6.50 |
| B1 | CERA CARNAUBA | 1.30 | 1.30 | 1.30 |
| B2 | BLACK IRON OXIDE | 8.00 | 8.00 | 8.00 |

The preparation process is the same as that described in the previous examples.

Measurement of Viscosity and of DH

Method of Measurement

It is identical to that described above.

Results

The values measured are presented in table 5 below.

The viscosity of the mascara of the invention is about 143 000 cPs, while that of the mascara containing triethanolamine stearate is about 165 000 cPs.

TABLE 5

Physicochemical characterization

|  | Example 4 | Comparative example 5 | Comparative example 6 |
|---|---|---|---|
| VISCOSITY (24 h) CPS | 143 000 | 165 000 | 200 900 |
| pH (24 h) | 8.29 | 7.92 | 8.59 |

Makeup Result

The results are presented in table 6 below.

TABLE 6

| Makeup and application qualities | | | |
|---|---|---|---|
| | Example 4 | Comparative example 5 | Comparative example 6 |
| CREAMY | ++ | +++ | − |
| VOLUME | ++ | ++ | + |
| EYELASH SUPPLENESS | ++ | ++ | + |
| ADHESION | +++ | ++ | + |

Legend:
−insufficient
+ medium result
++ very good
+++ excellent

Nitrosamine Assay

Method of Measurement

The two formulas are conditioned in a 120 mL pill bottle and left to stand for 6 months in an incubator at a temperature of 40° C., with the assay carried out according to standard ISO 15819:2014.

Results

The values measured are presented in table 7 below.

TABLE 7

| Nitrosamine assay | | | |
|---|---|---|---|
| Conditions | Example 4 | Comparative example 5 | Comparative example 6 |
| 6 months at 20° C. | <10 ppb | 19 ppb | 65 ppb |
| 6 months at 40° C. | <10 ppb | 237 ppb | <10 ppb |

The NDLEA content is compliant (that is to say less than 10 ppb at 20° C. and 40° C.) after 6 months of storage for the formula of the invention, whereas it is greater than 20 ppb for the comparative formula containing triethanolamine stearate.

The invention claimed is:

1. A cosmetic composition for caring for or making up the eyelashes or the eyebrows, comprising a mixture of waxes in emulsion in an aqueous phase and at least one ester obtained by reacting a linear and saturated fatty acid comprising from 16 to 20 carbon atoms and tetrahydroxypropyl ethylenediamine, the mole ratio between the fatty acid and the amine being between 0.9 and 5, the fatty acid representing from 2.0 to 8.0% by weight and the amine representing from 0.1 to 8.0% by weight, relative to the weight of the composition.

2. The composition as claimed in claim 1 wherein the fatty acid is at least one selected from the group consisting of palmitic acid, stearic acid and behenic acid.

3. The composition as claimed in claim 1, comprising a mixture of an ester of stearic acid and of tetrahydroxypropyl ethylenediamine, and an ester of palmitic acid and of tetrahydroxypropyl ethylenediamine.

4. The composition as claimed in claim 1, wherein the waxes represent from 10 to 35% by weight relative to the weight of the composition.

5. The composition as claimed in claim 1, wherein the mixture of waxes comprises a first wax with a melting point greater than or equal to 70° C., and a second wax with a melting point less than 70° C., one of the first and second waxes being an alkane wax and the other being a polar wax.

6. The composition as claimed in claim 1, having a viscosity of the composition between 140 000 mPa·s and 210 000 mPa·s.

7. The composition as claimed in claim 1, wherein the composition comprises at least one nonionic surfactant having an HLB less than 8.

8. The composition as claimed in claim 1, wherein the composition comprises at least one nonionic surfactant having an HLB greater than 8.

9. The composition as claimed in claim 1, wherein the composition contains between 40 and 55% by weight of water.

10. A process for making up the eyelashes or the eyebrows which comprises applying to the eyelashes or the eyebrows a composition as claimed in claim 1.

11. The composition as claimed in claim 3, wherein the two esters are present in equal weight amounts.

12. The composition as claimed in claim 7, wherein the at least one nonionic surfactant having an HLB less than 8 comprises at least one selected from the group consisting of glyceryl stearate and the compound with the INCI name Steareth-2.

13. The composition as claimed in claim 8, wherein the at least one nonionic surfactant having an HLB greater than 8 comprises the compound with the INCI name Steareth-20.

* * * * *